US00PP09872P

United States Patent [19]

Zaiger et al.

[11] Patent Number: Plant 9,872

[45] Date of Patent: Apr. 29, 1997

[54] PEACH TREE "AUTUMN SNOW"

[76] Inventors: Chris F. Zaiger, 929 Grimes Ave.; Gary N. Zaiger, 1907 Elm Ave.; Leith M. Gardner, 1207 Grimes Ave.; Grant G. Zaiger, 4005 California Ave., all of Modesto, Calif. 95358

[21] Appl. No.: 599,124

[22] Filed: Feb. 9, 1996

[51] Int. Cl.[6] ..... A01H 5/00

[52] U.S. Cl. ..... Plt./42.1

[58] Field of Search ..... Plt./42.1

*Primary Examiner*—James R. Feyrer

[57] ABSTRACT

A new and distinct variety of peach *Prunus persica* tree; its novelty consists of the following unique combination of desirable features:

1. A heavy and regular bearer of fruit.
2. Fruit with excellent flavor and eating quality.
3. Bearing large, firm, white flesh, freestone fruit.
4. Fruit with a high degree of attractive orange-red skin color.
5. Fruit with good handling and shiping quality.
6. Vigorous, upright growth.

1 Drawing Sheet

ORIGIN OF THE VARIETY

The present new and distinct variety of peach tree was originated by us in our experimental orchard located near Modesto, Calif., as a first generation cross between two selected seedlings with field identification numbers 107ED101 and 97GF518. Both the seed parent (107ED101) and the pollen parent (97GF518) originated as open pollinated Snow Giant Peach (U.S. Plant Pat. No. 8,085) seedlings. A large group of these first generation seedlings were grown under careful observation, during which time the present variety exhibited the desirable fruit characteristics described above and was selected for asexual propagation and commercialization.

ASEXUAL REPRODUCTION OF THE VARIETY

The present variety of peach tree was asexually reproduced by budding, as performed by us in our experimental orchard located near Modesto, Calif., and shows that all characteristics come true to form and are established and transmitted through succeeding asexual propagations.

SUMMARY OF THE VARIETY

The herein described new and distinct variety of peach tree is of large size, vigorous, upright growth, and a productive and regular bearer of large, firm, white flesh, freestone fruit with excellent flavor and eating quality. The fruit is further characterized by being relatively uniform in size throughout the tree; having firm flesh with good handling and shipping quality; having a high degree of attractive orange-red skin color and ripening in the late maturity season, approximately 6 to 7 days after Snow Giant peach (U.S. Plant Pat. No. 8,085).

DESCRIPTION OF THE PHOTOGRAPH

The accompanying photographic illustration shows typical specimens of the fruit and foliage of the present new variety of peach tree, with the upper and lower surface of the leaves, an exterior and sectional view of the fruit, with one fruit being divided in the suture plane to reveal flesh coloration, pit cavity and a stone remaining in place. The photographic illustration was taken shortly after being picked (firm ripe) and the colors are as nearly true as is reasonably possible in a color representation of this type.

DESCRIPTION OF THE VARIETY

The botanical details of the new and distinct variety of peach tree, its flowers, foliage and fruit are base on observations of specimens grown in our experimental orchard located near Modesto, Calif., with color terminology (except those in common terms) in accordance with Reinhold Color Altas by A. Kornerup and J. H. Wanscher.

Tree:
- *Size.*—Large.
- *Vigor.*—Vigorous.
- *Growth.*—Upright.
- *Density.*—Medium dense.
- *Productivity.*—Productive.
- *Bearing.*—Regular.

Trunk:
- *Size.*—Medium to large.
- *Texture.*—Medium shaggy.
- *Color.*—Brown to coffee brown (5-E-5) to (5-E-6).

Branches:
- *Size.*—Medium.
- *Texture.*—Medium rough.
- *Lenticels.*—Medium number. Medium size.
- *Color.*—Tan to dull brown, varies with age of growth.

Leaves:
- *Size.*—Large. Average length — 5½". Average width — 1¼".
- *Form.*—Lanceolate, pointed.
- *Texture.*—Smooth.
- *Margin.*—Serrulate.
- *Petiole.*—Size — medium. Average length — ½". Medium thickness.
- *Glands.*—Reniform. Number varies from 1 to 3. Average number 2. Located on lower portion of leaf blade and upper portion of petiole.

Flower buds:
- *Size.*—Medium to large.
- *Length.*—Medium.
- *Form.*—Plump, free.

Flowers:
- *Size.*—Large, showy.
- *Blooming period.*—Date of first bloom: Mar. 2, 1994. Date of full bloom: Mar. 8, 1994. Varies slightly with climatic conditions.
- *Pollen.*—Present, self fertile.

*Color.*—Pink to rose pink, slightly darker pink than normal peach flowers. Some flowers have an extra petal or petaloids.

Fruit:

*Maturity when described.*—Firm ripe.

*Date of first picking.*—Aug. 13, 1994.

*Date of last picking.*—Aug. 20, 1994.

*Size.*—Large. Comparatively uniform. Average diameter axially 3¼". Average transversely in suture plane 3⅜".

*Form.*—Nearly globose, flattened at stem end and slight apical point on some fruit.

*Suture.*—Shallow, extends from base to apex.

*Ventral surface.*—Usually rounded, nearly smooth.

*Base.*—Retuse.

*Apex.*—Varies from slight apical point to rounded.

*Cavity.*—Rounded, slighytly elongated in suture plane. Average depth ⅝". Average breath 1".

Flesh:

*Texture.*—Firm.

*Ripens.*—Evenly.

*Juice.*—Moderate.

*Flavor.*—Excellent, mild, sweet, sub-acid.

*Eating quality.*—Excellent.

*Fibers.*—Few, very small, tender.

*Amygdalin.*—Undetected.

*Aroma.*—Moderate.

*Color.*—White to pinkish white (6-A-1) to (6-A-2). Pit cavity, red to cardinal red (10-C-8) to (10-D-8). Red extending into flesh from pit cavity.

Skin:

*Thickness.*—Medium.

*Texture.*—Medium tough, tenacious to flesh.

*Tendency to crack.*—None.

*Down.*—Moderate, short to medium length.

*Color.*—Overspread with orange-red to lake red (9-C-6) to (9-C-8). White to yellowish white ground color (4-A-1) to (4-A-2).

Stone:

*Type.*—Freestone.

*Size.*—Medium to large. Average length — 1¼". Average breadth — ⅞". Average thickness — ¾".

*Form.*—Oval to ovoid.

*Base.*—Usually straight, varies from straight to rounded.

*Apex.*—Acuminate to cuspidate.

*Sides.*—Equal to unequal.

*Tendency to split.*—None.

*Surface.*—Irregularly furrowed toward apex, pitted toward base. Pits vary from round to elongated, some with slight callus.

*Color.*—Brown to reddish brown (10-E-7) to (10-E-8).

Use: Dessert.

*Market.*—Local and long distance.

Keeping quality: Good.

Shipping quality: Good.

The new variety of peach tree, its flowers, foliage and fruit may vary in slight detail due to climate, soil conditions and cultural practices under which the variety may be grown. The present botanical description is that of the variety grown under the ecological conditions prevailing near Modesto, Calif.

We claim:

1. A new and distinct variety of peach tree, substantially as illustrated and described, characterized by its large size, vigorous, upright growth and a productive and regular bearer of large, white flesh, freestone fruit with excellent flavor and eating quality; the new variety is further characterized by having firm flesh with good handling and shipping quality, having a high degree of attractive orange-red skin color, ripening in the late maturity season, approximately 6 to 7 days after Snow Giant Peach (U.S. Plant Pat. No. 8,085).

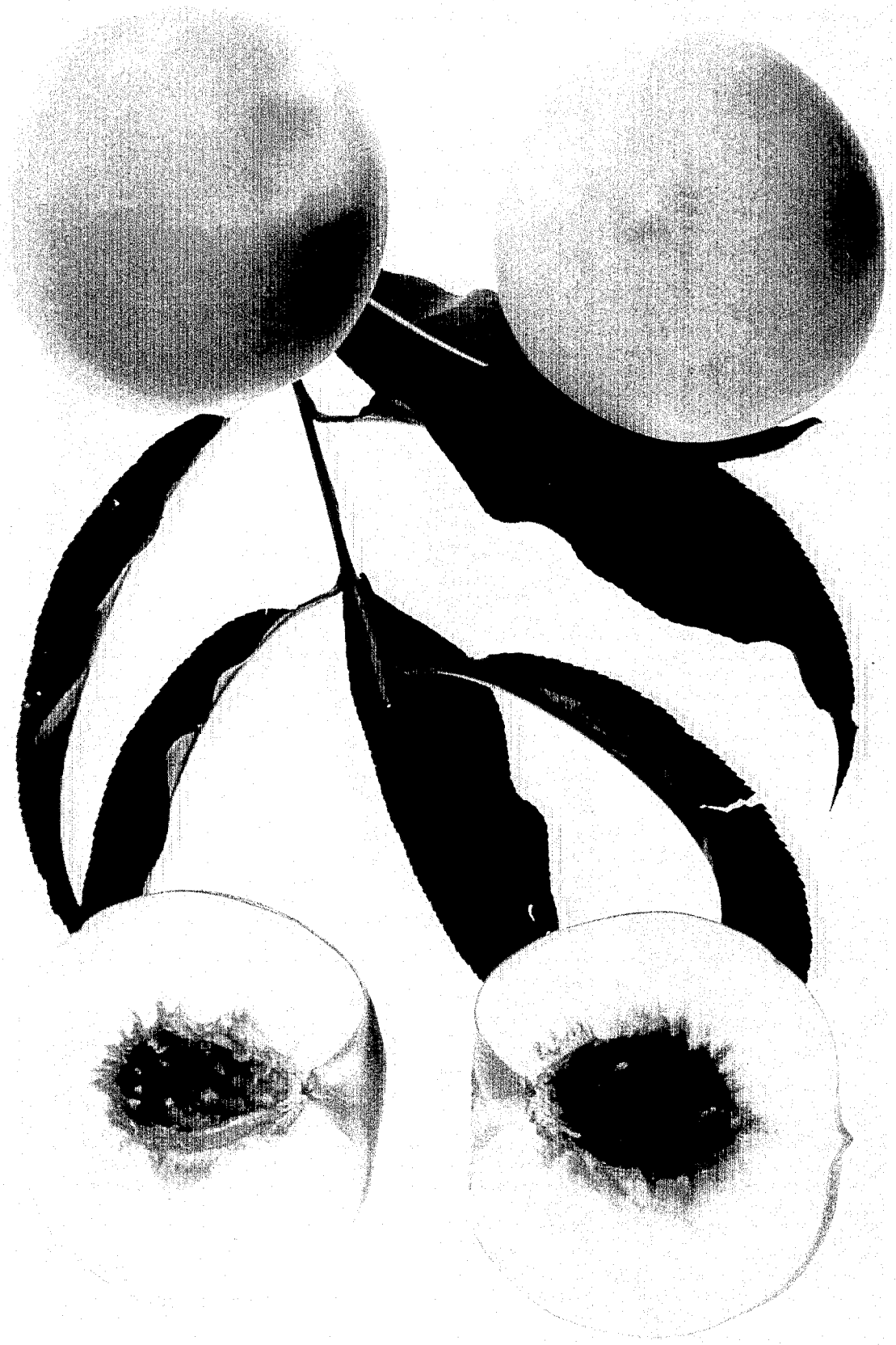

* * * * *